United States Patent
Feldman et al.

(10) Patent No.: US 10,524,493 B2
(45) Date of Patent: Jan. 7, 2020

(54) COMPOSITIONS AND METHODS FOR PREVENTING OR RELIEVING SYMPTOMS OF INFECTIONS

(71) Applicant: The Johns Hopkins University, Baltimore, MD (US)

(72) Inventors: Andrew B. Feldman, Columbia, MD (US); Jeffrey S. Lin, Silver Spring, MD (US); Kellogg Schwab, Bel Air, MD (US); Timothy Julian, Baltimore, MD (US); Christiane Wobus, Dexter, MI (US); David Weitz, Bolton, MA (US); John Heyman, Somerville, MA (US)

(73) Assignee: The Johns Hopkins University, Baltimore, MD (US)

( * ) Notice: Subject to any disclaimer, the term of this patent is extended or adjusted under 35 U.S.C. 154(b) by 322 days.

(21) Appl. No.: 14/487,592

(22) Filed: Sep. 16, 2014

(65) Prior Publication Data

US 2015/0079115 A1    Mar. 19, 2015

Related U.S. Application Data

(60) Provisional application No. 61/878,073, filed on Sep. 16, 2013.

(51) Int. Cl.
   *C07K 16/10*    (2006.01)
   *A61K 39/00*    (2006.01)
   *A23L 33/135*    (2016.01)

(52) U.S. Cl.
   CPC ............ *A23L 33/135* (2016.08); *C07K 16/10* (2013.01); *A23Y 2220/17* (2013.01); *A61K 39/00* (2013.01)

(58) Field of Classification Search
None
See application file for complete search history.

(56) References Cited

U.S. PATENT DOCUMENTS

| | | | | |
|---|---|---|---|---|
| 8,841,120 | B2* | 9/2014 | Richardson | A61K 39/12 435/320.1 |
| 2007/0280949 | A1* | 12/2007 | Alfa | A61K 35/744 424/157.1 |
| 2009/0226418 | A1* | 9/2009 | Frenken | A23G 9/363 424/130.1 |
| 2011/0195113 | A1* | 8/2011 | Richardson | A61K 39/12 424/450 |
| 2014/0271712 | A1* | 9/2014 | Baric | C07K 14/005 424/216.1 |
| 2015/0079115 | A1* | 3/2015 | Feldman | A23L 1/3014 424/178.1 |
| 2015/0093744 | A1* | 4/2015 | Tian | C12Q 1/6806 435/5 |
| 2017/0088821 | A1* | 3/2017 | Karst | C12Q 1/701 |

FOREIGN PATENT DOCUMENTS

WO    WO 2006/056306    * 6/2006

OTHER PUBLICATIONS

Palladino et al, Journal of Virology, Apr. 1995, p. 2075-2081 vol. 69, No. 4.*
Arias et al, Future Microbiol. (2013) 8(11), 1475-1487.*
Wobus et al, J. Virology, Jun. 2006, p. 5104-5112, vol. 80, No. 11.*
Richardson et al, Expert Rev. Vaccines, 2013, 12/2:155-167.*
Cannon et al, J. Virology, Jun. 2009, 83/11:5363-5374.*
Hoang et al, Appl. Microbiol. Biotechnol., 2015, 99:2793-2803.*
LoBue et al, Vaccine, 2006, 24:5220-5234.*
Czerkinsky et al, Current Topics in Mircobiology and Immunology, 2012, 354:1-18.*
Kim et al, J. Medicinal Chemistry, 2015, 58:9438-9450.*
Harlow et al In Antibodies A Laboratory Manual, Cold Spring Harbor Press, 1988, Chapter 3, pp. 23-35.*
Greenbaum et al, Journal of Molecular Recognition, 20(2):75-82, 2007.*
Greenspan et al, Nature Biotechnology 17:936-937, 1999.*
Cardemil et al, Infect Dis Clin N Am, 31 (2017) 839-870. (Year: 2017).*
Pant, Neha et al., "Lactobacilli Expressing Variable Domain of Llama Heavy-Chain Antibody Fragments (Lactobodies) Confer Protection against Rotavirus-Induced Diarrhea," The Journal of Infectious Diseases, vol. 194, Issue 11, Oct. 23, 2006, pp. 1580-1588.
Pouwels, P.H. et al., "Lactobacilli as Vehicles for Targeting Antigens to Mucosal Tissues by Surface Exposition of Foreign Antigens," Methods in Enzymology, vol. 336, pp. 369-389 (2001).

\* cited by examiner

*Primary Examiner* — Nita M. Minnifield
(74) *Attorney, Agent, or Firm* — Noah J. Hayward

(57) ABSTRACT

Food products and/or pharmaceutical preparations including (i) viral neutralizing antibodies or antibody fragments anchored to a probiotic microorganism and (ii) a carrier medium for delivering the viral neutralizing antibodies or antibody fragments anchored to probiotic microorganisms to the gut of a mammal. Also provided are methods of making food products and/or pharmaceutical preparations, which can be used to treat existing viral infections or prevent the spread or transmission of viral infection.

9 Claims, 4 Drawing Sheets

Untransformed
Lactobacilli

Bound Rotavirus

Lactobacilli expressing
surface-anchored VHH1
binding of rotavirus

COMPOSITIONS AND METHODS FOR PREVENTING OR RELIEVING SYMPTOMS OF INFECTIONS

CROSS-REFERENCE TO RELATED APPLICATIONS

This application claims priority to and the benefit of U.S. Provisional Application Ser. No. 61/878,073 filed on Sep. 16, 2013, the entire contents of which are hereby incorporated herein by reference.

STATEMENT OF GOVERNMENTAL INTEREST

This invention was made with government support under contract number 123723-5043735 awarded by the Defense Advanced Research Projects Agency (DARPA). The government has certain rights in the invention.

TECHNICAL FIELD

The presently disclosed subject matter is related to food products and pharmaceutical preparations for the prophylactic or therapeutic management of viral infections and a method for rapid production of these food products and pharmaceutical preparations.

BACKGROUND

Antibodies (also called immunoglobulins) are glycoproteins, which specifically recognize foreign molecules. These recognized foreign molecules are called antigens. When antigens invade humans or animals, an immunological response is triggered which involves the production of antibodies by B-lymphocytes. By this immunological response, microorganisms, larger parasites, viruses and bacterial toxins can be rendered harmless. The unique ability of antibodies to specifically recognize and bind with high affinity to virtually any type of antigen makes them useful molecules in medical and scientific research.

In vertebrates five immunoglobulin classes are described, including IgG, IgM, IgA, IgD and IgE, all of which differ in their function in the immune system. IgGs are the most abundant immunoglobulins in the blood. They have a basic structure of two identical heavy (H) chain polypeptides and two identical light (L) chain polypeptides. The H and chains are kept together by disulfide bridges and non-covalent bonds. The chains themselves can be divided in variable and constant domains. The variable domains of the heavy and light chain ($V_H$ and $V_L$), which are extremely variable in amino acid sequences, are located at the N-terminal part of the antibody molecule. $V_H$ and $V_L$ together form the unique antigen-recognition site. The amino acid sequences of the remaining C-terminal domains are much less variable and are called $C_H1$, $C_H2$, $C_H3$ and $C_L$. The non-antigen binding part of an antibody molecule is called the constant domain Fc and mediates several immunological functions, such as binding to receptors on target cells and complement fixation.

The unique antigen-binding site of an antibody consists of the heavy and light chain variable domains ($V_H$ and $V_L$). Each domain contains four framework regions (FR) and three regions called CDRs (complementarity determining regions) or hypervariable regions. The CDRs strongly vary in sequence and determine the specificity of the antibody. $V_L$ and $V_H$ domains together form a binding site, which binds a specific antigen.

Exemplary foreign bodies include a wide variety of viruses, such as norovirus. Norovirus, for example, is a genus of genetically diverse single-stranded RNA, non-enveloped viruses in the Caliciviridae family. The known viruses in the genus are all considered to be the variant strains of a single species called Norwalk virus. The viruses are known to be transmitted by fecally contaminated food or water, by person-to-person contact, and via aerosolization of the virus and subsequent contamination of surfaces. Noroviruses are the most common cause of viral gastroenteritis in humans and affect people of all ages.

Norovirus infection is characterized by nausea, forceful vomiting, watery diarrhea, abdominal pain, and in some cases, loss of taste. General lethargy, weakness, muscle aches, headache, and low-grade fever may occur. The disease is usually self-limiting, and severe illness is rare. Although having norovirus can be unpleasant, it is not usually dangerous and most individuals that contract it make a full recovery within a couple of days. However, the virus affects around 267 million people and causes over 200,000 deaths each year.

After infection, immunity to norovirus is usually incomplete and temporary. Outbreaks of norovirus infection often occur in closed or semiclosed environments, such as long-term care facilities, overnight camps, hospitals, schools, prisons, dormitories, and cruise ships, where the infection spreads very rapidly either by person-to-person transmission or through contaminated food. For example, many norovirus outbreaks have been traced to food that was handled by one infected person.

Moreover, viruses (e.g., norovirus) can often evolve or mutate over time. In some cases the evolution of viruses can occur rather rapidly, which makes screening, identification and distribution of neutralizing antibodies in a timely and cost-effective manner particularly difficult.

Accordingly, there remains a need for a cost-effective and timely approach to maintain efficacy of therapeutic antibodies as viruses (e.g., norovirus) evolve.

BRIEF SUMMARY

Example embodiments of the present invention may address one or more of the aforementioned remaining needs. For instance, certain embodiments according to the present invention provide a transformed probiotic microorganism (e.g., bacteria) including viral neutralizing antibodies or antibody fragments anchored thereon and/or are configured to express (e.g., secrete or produce) the viral neutralizing antibodies or antibody fragments. In certain embodiments, for instance, the transformed probiotic microorganism includes viral neutralizing antibodies or antibody fragments anchored onto the surface of the transformed probiotic microorganism. In certain embodiments, the viral neutralizing antibodies or antibody fragments can exhibit a binding affinity (e.g., a specific binding affinity) for any particular or desired virus. For instance, the viral neutralizing antibodies or antibody fragments can include a unique antigen-recognition site that specifically binds to a particular (or desired) virus. In accordance with certain embodiments, for example, the viral neutralizing antibodies or antibody fragments comprise norovirus (e.g., HuNoV) neutralizing antibodies or antibody fragments.

In other embodiments, the present invention provides a food product or pharmaceutical preparation (e.g., vaccine) configured and suitable for the management of viral infections. In certain embodiments, for instance, the food product or pharmaceutical preparation can comprise viral neutralizing antibodies or antibody fragments anchored to a probiotic microorganism and a carrier medium for delivering these viral neutralizing antibodies or antibody fragments anchored to probiotic microorganisms to the gut of a subject (e.g., a mammal).

In other embodiments, the present invention includes a method for making a food product or pharmaceutical preparation. In accordance with certain embodiments, the method can comprise isolating a virus from infected mammals (e.g., humans) and inoculating mice (or other animals) with the isolated virus. After inoculation, murine cells can be isolated from one or more murine tissues followed by sorting the murine cells and identifying cells that bind to the virus of interest. After identification, a step of sequencing murine viral neutralizing antibody genes derived from the murine cells that bind to the virus can be performed. Methods according to example embodiments of the present invention can also include a step of transforming a probiotic microorganism (e.g., bacteria) such that it expresses the viral neutralizing antibodies or antibody fragments on its surface (e.g., on the surface of the probiotic microorganism) and adding the transformed probiotic microorganism during the manufacture of the food product or pharmaceutical preparation. In this regard, the transformed probiotic microorganism can be considered as an additional ingredient to the food product or pharmaceutical preparation.

Example embodiments of the present invention provide many advantages. For example, the method for making a food product or pharmaceutical preparation of the present invention can permit the rapid isolation of antibody secreting cells and rapid, high-throughput screening for neutralizing antibodies, which enables a more rapid turnaround of neutralizing antibodies for viruses that mutate rapidly, thereby permitting a cost-effective and timely approach to maintain efficacy of therapeutic antibodies as viruses evolve. In this regard, for example, example embodiments of the present invention also provide methods of preventing viral infections and/or methods of treating existing viral infections (e.g., norovirus infections). In such methods, for example, a mammal (e.g., human) can be administered a food product or pharmaceutical preparation according to example embodiments of the present invention. In certain embodiments, the food product or pharmaceutical preparation can be administered to a mammal already exhibiting symptoms of viral infection as a means of treating such a viral infection, while the food product or pharmaceutical preparation can be administered to a mammal not yet exhibiting any symptoms of viral infection as a means of preventing a viral infection. In this regard, the food product or pharmaceutical preparation can be employed both actively against a current viral infection (e.g., as a therapeutic) or prophylatically.

BRIEF DESCRIPTION OF THE DRAWINGS

Example embodiments of the present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

FIG. 1A shows untransformed lactobacilli.
FIG. 1B shows lactobacilli expressing surface-anchored VHH1 binding of rotavirus according to certain embodiments of the present invention.

DETAILED DESCRIPTION

Figure 2:
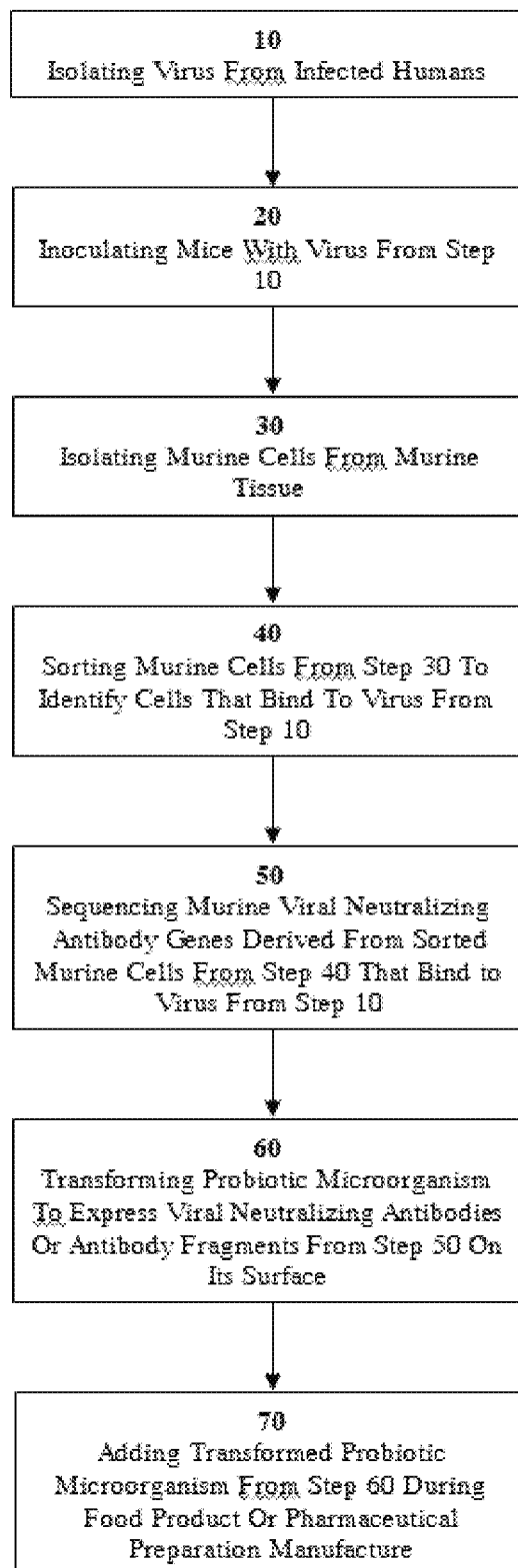
FIG. 2 illustrates a flow diagram according to certain embodiments of the present invention.

Example embodiments of the present invention now will be described more fully hereinafter with reference to the accompanying drawings, in which some, but not all embodiments of the inventions are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used herein, the terms "antibody" and "antibodies" refer to a glycoprotein substantially encoded by an immunoglobulin gene or immunoglobulin genes, or fragments thereof, which specifically recognize and bind foreign molecules called antigens. The recognized immunoglobulin genes include the kappa, lambda, alpha, gamma, delta, epsilon, and mu constant region genes, as well as the immunoglobulin variable region genes. Antibodies include fragments, such as Fab', F(ab)$_2$, Fabc, and Fv fragments. Fab fragments are the antigen-binding domains of an antibody molecule. Fab fragments can be prepared by papain digestions of whole antibodies. Fv fragments are the minimal fragment (~30 kDa) that still contains the whole antigen-binding site of a whole IgG antibody. Fv fragments are composed of both the variable heavy chain ($V_H$) and variable light chain ($V_L$) domains. This heterodimer, called Fv fragment (for fragment variable) is still capable of binding the antigen. The term "antibody," as used herein, also includes antibody fragments either produced by the modification of whole antibodies or those synthesized de novo using recombinant DNA methodologies, and further includes "humanized" antibodies made by now conventional techniques.

As used herein, "carrier medium" refers to a consumable food or beverage (or a food additive (e.g., a powder, liquid, and/or the like) that may be added to a food or beverage) frequently used in conjunction with probiotic microorganisms. Examples of consumable foods or beverages include, but are not limited to, yogurt; meat products such as sausage; brined vegetables such as sauerkraut, carrots, olives, or beets; margarines and other spreads; frozen confectionary products such as ice cream, frozen yogurt, sherbet, sorbet, ice milk, frozen custard, popsicles, granitas, or frozen fruit purees; fruit juices; soft drinks; tea-based products such as tea bags, leaf tea, herbal tea bags, herbal infusions, powdered tea, powdered herbal tea, iced tea, iced herbal tea, carbonated iced tea, or carbonated iced herbal tea; meal replacement drinks; salad dressings or mayonnaise; meal replacer snacks or bars; and dry lemonade powder. As mentioned above, other additives or powders may also be employed.

As used herein, "probiotic microorganism" refers to viable microbial food supplements which beneficially influence the host by improving its intestinal microbial balance.

In accordance with certain embodiments of the present invention, the probiotic microorganism should be able to survive passage in the gastrointestinal tract (GIT) and should be active in the gut. In certain embodiments, the microorganism may be able to undergo transient colonization of the GIT; be able to express the gene in the GIT; and be able to stimulate the gut immune system. If the probiotic microorganism is a bacterium, a lactic acid bacterium can be particularly desirable according to certain embodiments of the present invention. Examples of other suitable probiotic microorganisms include yeast such as *Saccharomyces, Debaromyces, Kluyveromyces* and *Pichia*, molds such as *Aspergillus, Rhizopus, Mucor* and *Penicillium* and bacteria such as the genera *Bifidobacterium, Propionibacterium, Streptococcus, Enterococcus, Lactococcus, Bacillus, Pediococcus, Micrococus, Leuconostoc, Weissella, Oenococcus* and *Lactobacillus. Kluyveromyces lactis* may also be used. Specific examples of suitable probiotic microorganisms include: *Kluyveromyces lactis, Kluyveromyces fragilis, Pichia pastoris, Saccharomyces cerevisiae, Saccharomyces boulardii, Aspergillus niger, Aspergillus oryzae, Mucor miehei, Bacillus subtilis, Bacillus natto, Bifidobacterium adolescentis, B. animalis, B. breve, B. bifidum, B. infantis, B. lactis, B. longum, Enterococcus faecium, Enterococcus faecalis, Escherichia coli, Lactobacillus acidophilus, L. brevis, L. casei, L. delbrueckii, L. fermentum, L. gasseri, L. helveticus, L. johnsonii, L. lactis, L. paracasei, L. plantarum, L. reuteri, L. rhamnosus, L. sakei, L. salivarius, L. sanfranciscus, Lactococcus lactis, Lactococcus cremoris, Leuconostoc mesenteroides, Leuconostoc lactis, Pediococcus acidilactici, P. cerevisiae, P. pentosaceus, Propionibacterium freudenreichii, Propionibacterium shermanii* and *Streptococcus salivarius*

Exemplary probiotic strains, for example, include: *Saccharomyces boulardii, Lactobacillus casei shirota, Lactobacillus casei immunitas, Lactobacillus casei* DN-114 001, *Lactobacillus rhamnosus* pk GG (ATCC53103), *Lactobacillus reuteri* ATCC55730/SD2112, *Lactobacillus rhamnosus* HN001, *Lactobacillus plantarum* 299v (DSM9843), *Lactobacillus johnsonii* La1 (I-1225 CNCM), *Lactobacillus plantarum* WCFS1, *Bifidobacterium lactis* HN019, *Bifidobacterium animalis* DN-173010, *Bifidobacterium animalis* Bb12, *Lactobacillus casei* 431, *Lactobacillus acidophilus* NCFM, *Lactobacillus reuteri* ING1, *Lactobacillus salivarius* UCC118, *Propionibacterium freudenreichi* JS, *Escherichia coli* Nissle 1917.

In accordance with certain embodiments, the probiotic microorganism can conveniently be a lactic acid bacterium. In certain embodiments, the probiotic microorganism is chosen from either *Lactobacillus* or bifidobacteria. In certain embodiments, the probiotic microorganism is *Lactobacillus*. Particularly, the *Lactobacillus* can comprise *Lactobacillus casei* 393 pLZ15. *Lactobacillus casei* has recently been re-identified as *Lactobacillus paracasei* (Perez-Martinez, 2003). Another *Lactobacillus* is *Lactobacillus reutarii*.

As used herein, "viral neutralizing antibody" refers to an antibody which binds to a site or multiple sites on a virus structure and subsequently inhibits the virus' ability to infect susceptible cells and tissues.

Although human norovirus (HuNoV) is frequently referenced throughout this disclosure, HuNoV serves only as an exemplary application of the present invention. The present invention, for example, can be applicable to a wide variety of enteric pathogens.

In one aspect, certain embodiments according to the present invention provide for the rapid screening for therapeutic antibodies against a variety of human viruses, such as noroviruses, using a unique murine culture model for human viruses, such as noroviruses. In certain embodiments according to the present invention droplet microfluidic technology can be utilized to rapidly isolate antibody secreting cells for obtained therapeutic, neutralizing antibody gene sequences. In accordance with certain embodiments, the identified antibody genes are introduced into a probiotic microorganism (e.g., bacteria) for use as an edible passive vaccine, in which the engineered/transformed bacilli populate the gut of a subject, capture pathogens on their surfaces, and/or secrete antibodies to opsonize (e.g., mark for destruction) the virus or viral proteins for subsequent destruction by phagocytic immune cells. The edible vaccine (e.g., food product or pharmaceutical preparation) can beneficially, for example, be consumed prophylatically (e.g., preventative applications), but in some cases could be used therapeutically (e.g., treatment of infection). In certain embodiments, the virus comprises a human norovirus. However, any other enteric pathogen other than human norovirus can be substituted according to certain embodiments of the present invention.

In accordance with certain embodiments, the present invention can beneficially provide rapid isolation of antibody secreting cells and rapid, high-throughput screening for neutralizing antibodies which enables a more rapid turnaround of neutralizing antibodies for viruses that mutate rapidly. As such, a cost-effective and timely approach to maintain efficacy of therapeutic antibodies as viruses evolve can be realized according to certain embodiments of the present invention. In this regard, certain embodiments of the present invention can provide therapeutics to prevent viral infections, such as norovirus infections, or relieve symptoms of viral infections, such as human norovirus infections. Certain embodiments of the present invention comprise isolating antibodies against circulating viruses (e.g., human noroviruses) using a unique mouse system to culture the viruses followed by inoculating a mouse (or other animal) to generate antibodies against the circulating viruses. In accordance with certain embodiments, the use of microfluidic cell isolation technology is utilized to obtain DNA sequences of the antibody genes. These sequences can then be introduced through genetic engineering into bacterial gene constructs to express the anti-noroviral, for example, antibodies on the surface of, for example, lactobacilli, which is a common probiotic bacteria in yogurts and a persisting denizen of the human gut. The lactobacilli, for example, can cull ingested viruses prior to an infection taking hold, relieve symptoms during an infection, and reduce transmission. Such methods, for example, can be used prophylactically as a tool to interdict an outbreak of a viral infection, such as norovirus, in high-transmission risk venues, for example, such as cruise ships, dormitories, or in nursing homes.

In one aspect, certain embodiments according to the present invention provide a transformed probiotic microorganism (e.g., bacteria) including viral neutralizing antibodies or antibody fragments anchored thereon and/or are configured to express (e.g., secrete or produce) the viral neutralizing antibodies or antibody fragments. In certain embodiments, for instance, the transformed probiotic microorganism includes viral neutralizing antibodies or antibody fragments anchored onto the surface of the transformed probiotic microorganism. In certain embodiments, the viral neutralizing antibodies or antibody fragments can exhibit a binding affinity (e.g., a specific binding affinity) for any particular or desired virus. For instance, the viral neutralizing antibodies or antibody fragments can include a unique antigen-recognition site that specifically binds to a particular (or desired) virus. In accordance with certain embodiments, for example, the viral neutralizing antibodies or antibody fragments comprise norovirus (e.g., HuNoV) neutralizing antibodies or antibody fragments.

In another aspect, the present invention provides a food product or pharmaceutical preparation (e.g., vaccine) configured and suitable for the management of viral infections. In certain embodiments, for instance, the food product or pharmaceutical preparation can comprise viral neutralizing antibodies or antibody fragments anchored to a probiotic microorganism and a carrier medium for delivering these viral neutralizing antibodies or antibody fragments anchored to probiotic microorganisms to the gut of a subject (e.g., a mammal). In accordance with certain embodiments, the probiotic microorganism can be configured or transformed to express viral neutralizing antibodies or antibody fragments, for example being surface-anchored to the probiotic microorganism, over a given period of time in the gut of a mammal.

Although the particular virus or enteric pathogen (and associated neutralizing antibodies or antibody fragments) of interest is not particularly limited according to embodiments of interest, the viral neutralizing antibodies or antibody fragments can comprise HuNoV neutralizing antibodies or antibody fragments. Additionally, the probiotic microorganism can be configured to produce HuNoV neutralizing antibodies or fragments thereof, such as while present in the gut of a mammal.

As discussed above, the probiotic microorganism according to certain embodiments of the present invention is not particularly limited. For example, any of the previously noted probiotic organisms can be utilized and/or included into food products or pharmaceutical preparations according to certain embodiments of the present invention. The probiotic microorganism according to certain embodiments, for instance, comprises a lactic acid bacterium. In certain embodiments, the probiotic microorganism comprises *Lactobacillus*. In certain embodiments, the *Lactobacillus* comprises *Lactobacillus casei*.

The carrier medium, according to certain embodiments of the present invention, is not particularly limited as long as the carrier medium does not interfere with the viability of the probiotic microorganism. For instance, the carrier medium can comprise a wide variety of consumable foods and beverages.

Several food products can be prepared according to certain embodiments of the present invention. The food products, for example, can be in the form of meal replacers, soups, noodles, ice-cream, sauces, dressing, spreads, cereals, beverages, bread, biscuits, other bakery products, sweets, bars, chocolate, chewing gum, dairy products, and dietetic products (e.g., slimming products or meal replacers). For some applications, food products according to certain embodiments of the present invention can also comprise dietary supplements.

Similarly, a wide variety of pharmaceutical preparations can be prepared according to embodiments of the present invention. Pharmaceutical preparations can be in the form, for example, of tablets (e.g., enteric coated for time and/or pH release), syrups, elixirs, solutions (e.g., drinkable, inhalable, etc.), and capsules.

The transformed probiotic microorganisms can be added during the manufacture of the food product or pharmaceutical preparation as viable cultured (wet) biomass or as a dried preparation, still containing viable micro-organisms.

The food product or pharmaceutical preparation, according to certain embodiments of the present invention, can comprise viral neutralizing antibodies or antibody fragments present in an effective amount to at least one of reduce duration, severity, or transmission of the virus of interest (e.g., HuNoV) in a subject consuming the food product or pharmaceutical preparation.

FIG. 1A shows untransformed Lactobacilli, while FIG. 1B shows Lactobacilli expressing surface-anchored VHH1 binding of rotavirus according to certain embodiments of the present invention. As illustrated by FIG. 1B, the rotavirus is beneficially bound to the surface of the Lactobacilli via a surface-anchored rotavirus neutralizing antibody.

In another aspect, the present invention provides methods for making food products or pharmaceutical preparations that can, for example, function as a vaccine. In accordance with certain embodiments, the method can comprise isolating a virus from infected mammals (e.g., humans) and inoculating mice (or other animals) with the isolated virus. After inoculation, murine cells can be isolated from one or more murine tissues followed by sorting the murine cells and identifying cells that bind to the virus of interest. After identification, a step of sequencing murine viral neutralizing antibody genes derived from the murine cells that bind to the virus can be performed. Methods according to embodiments of the present invention can also include a step of transforming a probiotic microorganism (e.g., bacteria) such that it expresses the viral neutralizing antibodies or antibody fragments on its surface (e.g., on the surface of the probiotic microorganism) and adding the transformed probiotic microorganism during the manufacture of the food product or pharmaceutical preparation. In this regard, the transformed probiotic microorganism can be considered as an additional ingredient to the food product or pharmaceutical preparation.

Methods, according to certain embodiments of the present invention, can be applicable to the prophylactic or therapeutic management of enteropathogenic microorganisms in general. Enteropathogenic microorganisms include, for example, viruses or enteropathogenic bacteria. Enteropathogenic bacteria may include, for example, *Salmonella, Campylobacter, E. coli* or *Helicobacter*. Enteropathogenic viruses may include, for example, Norovirus (Norwalk-like virus), enteric adenovirus, Coronavirus, astroviruses, caliciviruses, and parvovirus. Rotavirus and the Norwalk family of viruses are the leading causes of viral gastroenteritis, however, a number of other viruses have been implicated in outbreaks (which can also be managed according to embodiments of the present invention). In certain embodiments, the present invention is directed to the management of noroviral infection and/or prevention of noroviral infection.

In certain embodiments, the present invention provides for the rapid screening for therapeutic antibodies against, for example, human noroviruses (HuNoV) using a unique murine culture model for HuNoV and utilizing droplet microfluidic technology to rapidly isolate antibody secreting cells to obtain neutralizing antibody gene sequences. These identified antibody genes are then introduced into probiotic microorganisms (e.g., bacteria) for use as an edible passive vaccine, for example, in which the engineered bacteria populate the gut, capture pathogens on their surfaces, and/or secrete antibodies to opsonize the virus or viral proteins for subsequent destruction by phagocytic immune cells.

In one embodiment of the present invention, HuNoV can be isolated from filtered human stool samples from confirmed HuNoV outbreaks. BALB/c Rag-γc-deficient mice can then be inoculated (e.g., intraperitoneally inoculated) with these filtered stool samples, and infection is allowed to develop for a desired period of time (e.g., 24 to 48 hours), at which point blood, spleen, and bone marrow tissues, for example, can be harvested and fecal samples collected. Using multiplex quantitative reverse transcriptase PCR (qRT-PCR), for example, HuNoV can be detected at high viral titers in fecal and tissue samples after the time period post infection (e.g., 24 to 48 hours). Although the period of time for allowance of infection references a time period of 24-48 hours, this time period can comprise at least any of the following: 1, 5, 10, 15, 20, 24, and 36 hours and/or at most about any of the following 72, 60, 50, 48, and 40 hours (e.g., 24-40 hours, 5-72 hours, etc.).

Antibody secreting cells can then be rapidly isolated using droplet microfluidic technology in order to obtain, for example, HuNoV neutralizing antibody gene sequences. Functional assays in a droplet microfluidics format using a sorter chip can isolate single mononuclear cells in blood and bone marrow, for example, which secrete HuNoV neutralizing antibodies. Compartmentalization of single cells in microfluidic droplets enables the analysis of proteins released from or secreted by cells. Secreted antibodies can be detected rapidly, for example, by co-compartmentalizing single mouse hybridoma cells, a fluorescent probe, and single beads coated with HuNoV neutralizing antibodies in droplets. The beads capture the secreted antibodies and, when the captured antibodies bind to the probe, the fluorescence becomes localized on the beads, generating a clearly distinguishable fluorescence signal that enables droplet sorting. The microfluidic system described can be easily adapted for screening other intracellular, cell-surface, or secreted proteins and for quantifying catalytic or regulatory activities.

After determining which antibodies bind to HuNoV, the HuNoV neutralizing antibody genes can be sequenced and engineered into bacteria. Techniques for synthesizing genes, incorporating them into micro-organism hosts, and expressing genes in micro-organisms are well known in the art, and the skilled person would readily be able to put the invention into effect using common general knowledge. The use of replicating or integrating vectors is contemplated. Specifically, the whole expression cassette can be inserted in a so-called "integration" plasmid, whereby the expression cassette will be integrated into the chromosome of the probiotic microorganism after transformation.

Non-limiting examples of nucleic acid sequencing techniques include, but are not limited to, chain terminator (Sanger) sequencing and dye terminator sequencing, as well as "second generation" sequencing techniques.

The so-called "second-generation sequencing" or "next-generation sequencing" (NGS) techniques have emerged as alternatives to Sanger and dye-terminator sequencing methods and can be beneficially utilized in certain embodiments according to the present invention. NGS methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing, template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $1\times10^6$ sequence reads can be achieved, resulting in up to 500 million base pairs (Mb) of sequence. In accordance with certain embodiments of the present invention, the methods of the present invention utilize pyrosequencing.

In the Solexa/Illumina platform (e.g., MiSeq sequencing platform), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

In accordance with certain embodiments, the microorganism can be transformed with an expression vector comprising the gene for the antibody of interest. The expression vector may contain a constitutive promoter in order to express the antibodies or fragments thereof. Such a constitutive promoter can support in situ expression of antibodies by transformed lactobacilli persisting (at least for a short period) in the intestinal tract after administration. Alternatively, the promoter can be chosen to be active only in the GIT and/or stomach/gut i.e. suitable for GIT specific expression only. This will ensure expression and/or secretion of the mouse heavy chain antibody or fragments thereof in the GIT, preferably the gut. Many constitutive promoters for lactobacilli are known in the art and an example of a promoter that is specifically inducible in the GIT is Pldh (Pouwels et al "Lactobacilli as vehicles for targeting antigens to mucosal tissues by surface exposition of foreign antigens" Methods in Enzymology (2001) 336:369-389).

The transformed/engineered probiotic microorganism (e.g., transformed with antibodies or fragments thereof) antibodies can be expressed and/or secreted, in accordance with certain embodiments, in the gut of a mammal. In this regard, the use of a probiotic microorganism as a means to express surface-anchored viral neutralizing antibodies or antibody fragments has the advantages that in vivo production of antibody fragments locally in the GIT circumvents the practical problem of degradation of orally administered antibodies in the stomach. Such a system based on probiotic microorganisms (e.g., bacteria) represents a safe and attractive approach to delivering antibodies specific to a particular virus to the GIT. Hence, the wide scale application of the lactobacilli expressing antibodies is relatively straightforward, requires minimal handling and storage costs, and is economical. Furthermore, the probiotic bacteria will remain in the gut for longer time duration and enable the constant production, according to certain embodiments, of the antibody to enable more constant protection against the enteropathogenic microorganism.

The engineered or transformed probiotic microorganisms (e.g., lactobacilli) can be added to a carrier medium during the manufacture of the food product, which can be consumed prophylactically or therapeutically as discussed above.

FIG. 2 illustrates a flow diagram according to certain embodiments of the present invention. As shown in FIG. 2, certain embodiments of the present invention include an initial isolating step 10, in which a virus from infected mammals (e.g., humans) is obtained. Next, an inoculating step 20 can be conducted, in which mice can be inoculated with the isolated virus from step 10. A murine cell isolation step 30 can then be conducted, in which murine cells can be isolated from one or more murine tissues. The murine cells can then be subjected to a sorting step 40 in which cells expressing antibodies that bind to the virus of interest are identified and separated from cells that do not express antibodies that bind to the virus of interest. Subsequent to step 40, a sequencing step is conducted on the murine viral neutralizing antibody genes derived from the murine cells that bind to the virus can be performed. In the embodiments illustrated by FIG. 2, the method also includes a transforming step 60 comprising genetically engineering a probiotic microorganism (e.g., bacteria) such that it expresses the viral neutralizing antibodies or antibody fragments on its surface (e.g., on the surface of the probiotic microorganism). The transformed probiotic microorganism from step 60 can then be added to a carrier medium, for example, during the manufacture of the food product or pharmaceutical preparation. In this regard, the transformed probiotic microorganism can be considered as an additional ingredient to the food product or pharmaceutical preparation.

Figure 3:
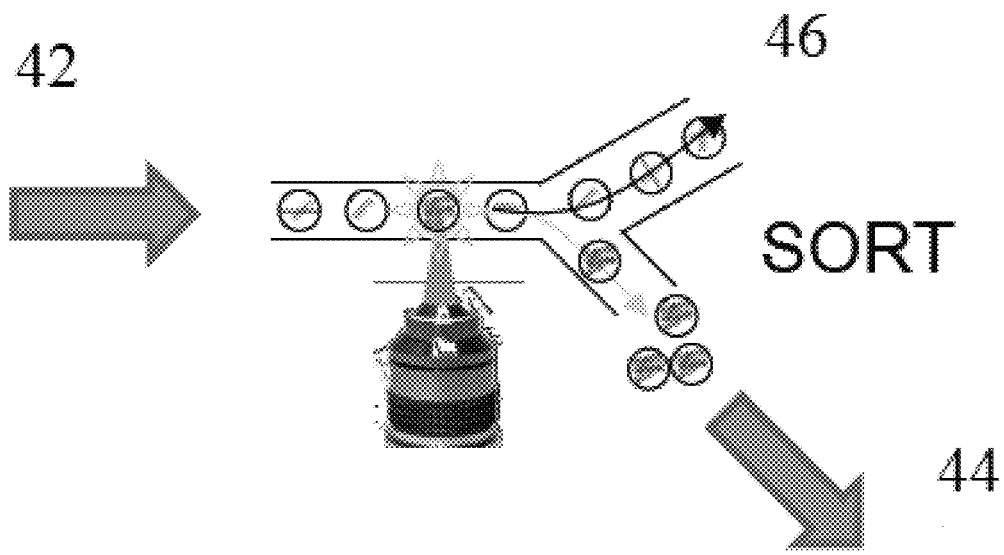
FIG. 3 illustrates a schematic for microfluidic sorting technology in which cells that secrete antibodies that bind the virus of interest (e.g., norovirus) are separated from other cells for subsequent sequencing.
Figure 4:
FIG. 4 illustrates a schematic for a sorter chip or sorting junction according to certain embodiments of the present invention.
Figure 5:
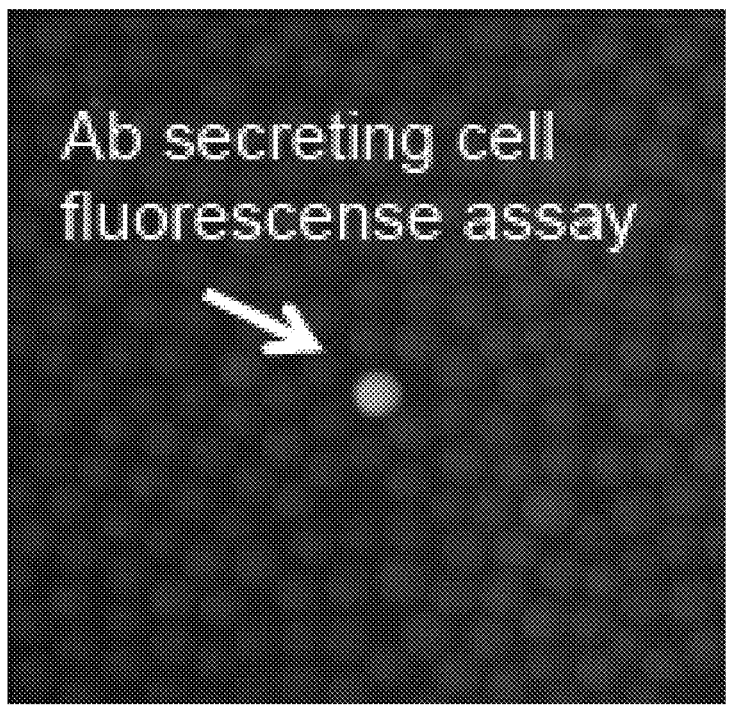
FIG. 5 shows an antibody-secreting cell fluorescence assay.

FIG. 3 illustrates a schematic for the droplet microfluidic technology according to certain embodiments of the present invention. As illustrated by FIG. 3 a mixture of cells 42 including (i) cells that express an antibody that binds to the virus of interest and (ii) cells that do not express an antibody that binds to the virus of interest. The droplet microfluidic-based sorter can identify and separate the individual microdroplets containing a cell that expresses an antibody that binds to the virus of interest and separate these cell-containing droplets into stream 44 from the droplets that contain cells that do not express an antibody that binds to the virus of interest and guide these droplets into stream 46. FIG. 4 illustrates a schematic for a sorter chip or sorting junction according to certain embodiments of the present invention. FIG. 5 shows an antibody-secreting cell fluorescence assay, in which an antibody secreting cell of interest is readily identified by fluorescence.

In another aspect, the present invention provides for methods of treating and/or preventing viral infections. In this regard, for example, certain embodiment of the present invention also provide methods of preventing viral infections and/or methods of treating existing viral infections (e.g., norovirus infections). In such methods, for example, a mammal (e.g., human) can be administered a food product or pharmaceutical preparation according to certain embodiments of the present invention. In certain embodiments, the food product or pharmaceutical preparation can be administered to a mammal already exhibiting symptoms of viral infection as a means of treating such a viral infection, while the food product or pharmaceutical preparation can be administered to a mammal not yet exhibiting any symptoms of viral infection as a means of preventing a viral infection. In this regard, the food product or pharmaceutical preparation can be employed both actively against a current viral infection (e.g., as a therapeutic) or prophylatically.

In certain embodiments according to the present invention, the method may comprise administering a food product or pharmaceutical preparation to reduce the duration, severity, and/or transmission of enteric pathogens, such as HuNoV infection. The food product or pharmaceutical preparation, according to certain embodiments, acts as a consumable (e.g., edible or drinkable) vaccine (e.g., active or passive) in which engineered bacteria populate the gut, capture pathogens on their surfaces, and/or secrete antibodies to opsonize the virus or viral proteins for subsequent destruction by phagocytic immune cells. Since the probiotic microorganism (e.g., bacteria) can remain in the gut for longer, it can enable the constant production, according to certain embodiments, of the desired antibody to enable more constant protection against the enteropathogenic microorganism. In certain embodiments, the food product or pharmaceutical preparation is administered (e.g., consumed by a mammal) prophylactically. Administration of the food product or pharmaceutical preparation, however, can also be used therapeutically to treat an existing viral infection and/or relieve symptoms associated with a particular viral infection.

These and other modifications and variations to the present invention may be practiced by those of ordinary skill in the art without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A food product or pharmaceutical preparation, comprising:
   (a) viral neutralizing antibodies or antibody fragments anchored to a probiotic microorganism, said viral neutralizing antibodies or antibody fragments comprise human norovirus (HuNoV) neutralizing antibodies or antibody fragments that exhibit a binding affinity to HuNoV isolated from confirmed HuNoV outbreaks; wherein the viral neutralizing antibodies or antibody fragments are derived from HuNoV inoculated BALB/c Rag-γ c-deficient mice from confirmed HuNoV outbreaks; and
   (b) a carrier medium for delivering said viral neutralizing antibodies or antibody fragments anchored to probiotic microorganisms to a gut of a mammal.

2. The food product or pharmaceutical preparation according to claim 1, wherein said probiotic microorganism is configured to produce human norovirus (HuNoV) neutralizing antibodies or fragments thereof.

3. The food product or pharmaceutical preparation according to claim 1, wherein said probiotic microorganism is a lactic acid bacterium.

4. The food product or pharmaceutical preparation according to claim 3, wherein said probiotic microorganism is *Lactobacillus*.

5. The food product or pharmaceutical preparation according to claim 4, wherein said *Lactobacillus* is *Lactobacillus casei*.

6. The food product or pharmaceutical preparation according to claim 1, wherein said carrier medium comprises a consumable food or beverage, or a food additive added to the consumable food or beverage.

7. The food product or pharmaceutical preparation according to claim 1, wherein said antibodies or antibody fragments are present in an effective amount to at least one of reduce duration, severity, or transmission of human norovirus (HuNoV) in a subject consuming said food product or pharmaceutical preparation.

8. A method of treatment, comprising: administering said food product or pharmaceutical preparation according to claim 1 to a subject in need thereof.

9. A process for preparing a food product or a pharmaceutical preparation, the food product or the pharmaceutical preparation comprising viral neutralizing antibodies or antibody fragments expressed on a surface of a probiotic microorganism and a carrier medium for delivering the viral neutralizing antibodies or antibody fragments expressed on the surface of the probiotic microorganism to a gut of a subject, the process comprising the following steps:
 (a) isolating a human norovirus (HuNoV) from infected humans;
 (b) inoculating BALB/c Rag-γc-deficient mice with said human norovirus (HuNoV);
 (c) isolating murine cells from a murine tissue;
 (d) sorting murine cells and identifying cells that bind to said human norovirus (HuNoV);
 (e) sequencing murine viral neutralizing antibody genes derived from said murine cells that bind to said human norovirus (HuNoV);
 (f) transforming the probiotic microorganism such that the probiotic microorganism expresses said viral neutralizing antibodies or antibody fragments on the surface of the probiotic microorganism; and
 (g) adding said transformed probiotic microorganism during the manufacture of the food product or the pharmaceutical preparation.

* * * * *